United States Patent [19]
Narayan

[11] Patent Number: 5,849,994
[45] Date of Patent: Dec. 15, 1998

[54] ANIMAL MODEL FOR HIV-1 INDUCED DISEASE

[75] Inventor: Opendra Narayan, Lake Quivira, Kans.

[73] Assignee: University of Kansas Medical Center, Kansas City, Kans.

[21] Appl. No.: 442,010

[22] Filed: May 16, 1995

[51] Int. Cl.$^6$ .......................... C12N 15/86; C12N 15/49; C12N 7/08; C12N 7/02

[52] U.S. Cl. .............................. 800/2; 435/237; 435/239; 435/320.1; 435/69.1; 435/69.3; 435/172.3; 435/91.2; 435/240.2; 424/9.2

[58] Field of Search ................................ 800/2; 435/237, 435/320.1, 69.3, 69.1, 172.3, 239, 240.2; 424/91.2, 9.2

[56] References Cited

PUBLICATIONS

Sakuragi, S. et al. (1992) "Infection of macaque monkeys with a chimeric human and simian immunodeficiency virus" *Journal of General Virology* 73:2983–2987.

Li, J. et al. (1992) "Infection of Cynomolgus Monkeys with a Chimeric HIV–1/SIV$_{mac}$ Virus That Expresses the HIV–1 Envelope Glycoproteins" *Journal of Acquired Immune Deficiency Syndromes* 5:639–646.

Shibata, R. and Adachi, A. (1992) "SIV/HIV Recombinants and Their Use in Studying Biological Properties" *AIDS Research and Human Retrviruses* 8(3):403–409.

Sharma, D.P. et al. (1992) "Derivation of Neurotropic Simian Immunodeficiency Virus from Exclusively Lymphocytetropic Parental Virus: Pathogenesis of Infection in Macaques" *Journal of Virology* 66(6):3550–3556.

Barnett, S.W. et al. (1994) "An AIDS–Like Condition Induced in Baboons by HIV–2" *Science* 266:642–646.

North, T.W. and LaCasse, R.A. (1995) "Testing anti–HIV drugs in the FIV model" *Nature Medicine* 1(5):410–411.

Desrosiers, R.C. (1990) "The Simian Immunodeficiency Viruses" *Annual Review of Immunology* 8:557–578.

Lewis and Johnson, 1995, "Developing animal models for AIDS research—progress and problems" *Trends in Biotechnology* 13:142–150.

Levy, J. A., *Journal of Medical Primatology*, vol. 25, pp. 163–174, 1996.

*Primary Examiner*—Jasemine C. Chambers
*Assistant Examiner*—Jill D. Schmuck
*Attorney, Agent, or Firm*—McDonnell Boehnen Hulbert & Berghoff

[57] ABSTRACT

HIV-1 does not cause disease in any non-human species. Thus, there is no animal model system to evaluate the efficacy of strategies aimed at preventing or ameliorating disease caused by this virus. The instant invention provides an animal model for HIV-1 induced disease, virus for generating such model animals, and methods for generating pathogenic SHIV.

11 Claims, 2 Drawing Sheets

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( i v ) ANTI-SENSE: NO ( i x ) FEATURE:
        ( A ) NAME/KEY: misc_feature
        ( B ) LOCATION: 1..27
        ( D ) OTHER INFORMATION: /note= "complementary to SIVmac239
            ( g p 1 2 0 ) 6565-6591"

( x i ) SEQUENCE DESCRIPTION: SEQ ID NO:1:

G G C T A A G G C T     A A T A C A T C T T     C T G C A T C                          2 7

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( i v ) ANTI-SENSE: YES ( i x ) FEATURE:
        ( A ) NAME/KEY: misc_feature
        ( B ) LOCATION: 1..27
        ( D ) OTHER INFORMATION: /note= "complementary to SIVmac239
            ( g p 1 2 0 ) 8179-8205"

( x i ) SEQUENCE DESCRIPTION: SEQ ID NO:2:

A C C C A A G A A C     C C T A G C A C A A     A G A C C C C                          2 7

( 2 ) INFORMATION FOR SEQ ID NO:3:

( i ) SEQUENCE CHARACTERISTICS:
        ( A ) LENGTH: 27 base pairs
        ( B ) TYPE: nucleic acid ( C ) STRANDEDNESS: single
                ( D ) TOPOLOGY: linear ( i i ) MOLECULE TYPE: other nucleic acid
                ( A ) DESCRIPTION: /desc = "PCR primer"

( i v ) ANTI-SENSE: NO ( i x ) FEATURE:
                ( A ) NAME/KEY: misc_feature
                ( B ) LOCATION: 1..27
                ( D ) OTHER INFORMATION: /note= "complementary to SIVmac239
                        ( g p 1 2 0 ) 6598-6624"

( x i ) SEQUENCE DESCRIPTION: SEQ ID NO:3:

GTAAGTATGG GATGTCTTGG GAATCAG                                                                27

( 2 ) INFORMATION FOR SEQ ID NO:4:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "PCR primer"

( i v ) ANTI-SENSE: YES ( i x ) FEATURE:
                ( A ) NAME/KEY: misc_feature
                ( B ) LOCATION: 1..27
                ( D ) OTHER INFORMATION: /note= "complementary to SIVmac239
                        ( g p 1 2 0 ) 8158-8184"

( x i ) SEQUENCE DESCRIPTION: SEQ ID NO:4:

GACCCCTCTT TTATTTCTTG AGGTGCC                                                                27

( 2 ) INFORMATION FOR SEQ ID NO:5:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "PCR primer"

( i v ) ANTI-SENSE: NO ( i x ) FEATURE:
                ( A ) NAME/KEY: misc_feature
                ( B ) LOCATION: 1..27
                ( D ) OTHER INFORMATION: /note= "complementary to HXBc2
                        ( g p 1 2 0 ) 6166-6192"

( x i ) SEQUENCE DESCRIPTION: SEQ ID NO:5:

CAAAGAAAAA TAGACAGGTT AATTGAT                                                                27

( 2 ) INFORMATION FOR SEQ ID NO:6:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "PCR primer"

( i v ) ANTI-SENSE: YES

-continued ( i x ) FEATURE:
    ( A ) NAME/KEY: misc_feature
    ( B ) LOCATION: 1..27
    ( D ) OTHER INFORMATION: /note= "complementary to HXBc2
        ( g p 1 2 0 ) 7810-7784"

( x i ) SEQUENCE DESCRIPTION: SEQ ID NO:6:

AGTGCTTCCT GCTGCTCCCA AGAACCC 27

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( i v ) ANTI-SENSE: NO ( i x ) FEATURE:
        ( A ) NAME/KEY: misc_feature
        ( B ) LOCATION: 1..30
        ( D ) OTHER INFORMATION: /note= "complementary to HXBc2
            ( g p 1 2 0 ) 6194-6223"

( x i ) SEQUENCE DESCRIPTION: SEQ ID NO:7:

GACTAATAGA AAGAGCAGAA GACAGTGGCA 30

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( i v ) ANTI-SENSE: YES ( i x ) FEATURE:
        ( A ) NAME/KEY: misc_feature
        ( B ) LOCATION: 1..27
        ( D ) OTHER INFORMATION: /note= "complementary to HXBc2
            ( g p 1 2 0 ) 7780-7754"

( x i ) SEQUENCE DESCRIPTION: SEQ ID NO:8:

GAACAAAGCT CCTATTCCCA CTGCTCT 27

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( i x ) FEATURE:
        ( A ) NAME/KEY: misc_feature
        ( B ) LOCATION: 1..24
        ( D ) OTHER INFORMATION: /note= "complementary to SIVmac239
            ( g a g ) 1052-1075"

( x i ) SEQUENCE DESCRIPTION: SEQ ID NO:9:

GATGGGCGTG AGAAACTCCG TCTT 24

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( i x ) FEATURE:
        ( A ) NAME/KEY: misc_feature
        ( B ) LOCATION: 1..28
        ( D ) OTHER INFORMATION: /note= "complementary to SIVmac239
            ( g a g ) 1423-1450"

( x i ) SEQUENCE DESCRIPTION: SEQ ID NO:10:

CCTCCTCTGC CGCTAGATGG TGCTGTTG                                            28

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( i x ) FEATURE:
        ( A ) NAME/KEY: misc_feature
        ( B ) LOCATION: 1..27
        ( D ) OTHER INFORMATION: /note= "complementary to B-actin
            gene"

( x i ) SEQUENCE DESCRIPTION: SEQ ID NO:11:

TCATGTTTGA GACCTTCAAC ACCCCAG                                              27

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( i x ) FEATURE:
        ( A ) NAME/KEY: misc_feature
        ( B ) LOCATION: 1..26
        ( D ) OTHER INFORMATION: /note= "complementary to B-actin
            gene"

( x i ) SEQUENCE DESCRIPTION: SEQ ID NO:12:

CCAGGAAGGA AGGCTGGAAG AGTGCC                                               26

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer"

( i x ) FEATURE:
        ( A ) NAME/KEY: misc_feature (B) LOCATION: 1..24
                (D) OTHER INFORMATION: /note= "complementary to SIVmac239
                    1142-1165"

(xi) SEQUENCE DESCRIPTION: SEQ ID NO:13:

GTTGAAGCAT GTAGTATGGG CAGC                                                                  24

(2) INFORMATION FOR SEQ ID NO:14:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "PCR primer"

(ix) FEATURE:
                (A) NAME/KEY: misc_feature
                (B) LOCATION: 1..24
                (D) OTHER INFORMATION: /note= "complementary to SIVmac239
                    1356-1382"

(xi) SEQUENCE DESCRIPTION: SEQ ID NO:14:

GCCTCAGGGC AGCGGAACCG CTCA                                                                  24

(2) INFORMATION FOR SEQ ID NO:15:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "PCR primer"

(ix) FEATURE:
                (A) NAME/KEY: misc_feature
                (B) LOCATION: 1..24
                (D) OTHER INFORMATION: /note= "complementary to B-actin
                    gene"

(xi) SEQUENCE DESCRIPTION: SEQ ID NO:15:

CCCCAGCCAT GTACGTTGCT ATCC                                                                  24

(2) INFORMATION FOR SEQ ID NO:16:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "PCR primer"

(ix) FEATURE:
                (A) NAME/KEY: misc_feature
                (B) LOCATION: 1..24
                (D) OTHER INFORMATION: /note= "complementary to B-actin
                    gene"

(xi) SEQUENCE DESCRIPTION: SEQ ID NO:16:

GCCTCAGGGC AGCGGAACCG CTCA                                                                  24

ANIMAL MODEL FOR HIV-1 INDUCED DISEASE

STATEMENT OF GOVERNMENT RIGHTS

This work was supported in part by NIH grant number NRR 06753, the Government of the United States of America may have rights in this invention.

FIELD OF THE INVENTION

The present invention relates to the field of animal model systems for human AIDS, and compositions and methods for generating them.

BACKGROUND OF THE INVENTION

It has long been recognized that it is desirable to have an accurate direct animal model for human AIDS (and HIV-1 induced disease) for testing of therapeutics and treatments. The inability of HIV-1 to cause disease in nonhuman species is a major impediment to understanding the mechanisms of pathogenesis of HIV-1 infection, and has stultified efforts to determine the efficacy of anti-HIV drugs and whether immune responses induced by HIV-1 proteins can protect against either infection or disease caused by this virus.

At present, HIV-2 infection of baboons and SIVmac infection in macaques are the best models of HIV-1 disease available (Barnett SW et al., 1994, *Science* 266: 1021–1029; Desrosiers RC, 1990, *Ann. Rev. Immunol.* 8: 557–578), but the genetic, antigenic, and structural differences in their env genes clearly distinguish these viruses from HIV-1. This is particularly evident in the V3 region of the HIV-1 env, which is highly variable and contains a linear neutralization epitope considered by many to be the major such epitope in the virus (Javaherian K, et al., 1989, *PNAS (USA)* 86: 6768–6772). The analogous regions in HIV-2 and SIVmac vary less and do not contain the major neutralization epitopes of these viruses (Robert-Guroff, M et al., 1992, *J. Virol.* 66: 3602–3608; Javaherian K, et al., 1992, *PNAS (USA)* 89: 1418–1422). The genetic and biological differences between the envelopes of HIV-1 and HIV-2/SIVmac are thus sufficient to preclude the latter as direct models of HIV-1, especially with respect to vaccine production and as a challenge virus for vaccines.

Other promising animal lentivirus models suffer from being of different evolutionary orders. Feline Immunodeficiency virus (FIV) has a similar effect on felines as HIV-1 does in humans, but it is not HIV-1 (North TW and LaCasse RA, 1995, *Nature Medicine* 1(5): 410–411). The SCID-hu mouse, a severe combined immunodeficient mouse transplanted with human hematopoietic cells, has also been used as an animal model for HIV-1 infection (Cavallo R et al., 1994, *Microbiologica* 17(3): 195–202).

The development of SIV-HIV chimeric viruses (SHIV), that bear the envelope of HIV-1 and are infectious in macaques, is a potential solution to the lack of an animal model of HIV-1 (Shibata R and Adachi A, 1992, *AIDS Res. Hum. Retroviruses* 8: 403–409; Sakuragi S. et al., 1992, *J. Gen. Virol.* 73: 2983–2987; Cheng-Mayer C et al., 1994, *Int. Conf. AIDS* 10: 61; Li J et al., 1992, *J. Aids* 5: 639–646; Yamamoto H et al., 1994, *Int. Conf. AIDS* 10: 75). However, SHIVs have not caused disease in macaques despite prolonged persistent infection (Igarashi T et al., 1994, *AIDS Res. Hum. Retroviruses* 10: 1021–1029).

The instant invention solves this problem by providing pathogenic SHIV which cause AIDS like syndrome in macaques, methods for the generation of pathogenic SHIV, and also providing methods and compositions for the production of an animal model for HIV-1 induced disease.

SUMMARY OF THE INVENTION

The instant invention provides compositions and methods for producing an animal model for HIV-1 infection that leads to development of AIDS.

The instant invention provides a monkey animal model for HIV-1 infection and AIDS, said monkey being treated by administering to the monkey viral isolate from bone marrow cells, the viral isolate being passaged at least two times previously through monkey bone marrow cells. In particular the instant invention provides a monkey animal model for HIV-1 infection and AIDS, said monkey being infected with a SHIV, made virulent by sequential passage three times through the bone marrow of selected monkeys. (The term "viral isolate", as used in this specification includes infective virus which is SHIV which has been passaged at least two times through bone marrow, SHIV infected bone marrow cells, and cell culture progeny of SHIV which has been passed at least two times through bone marrow.)

In a preferred embodiment, the instant invention provides for a monkey animal model for HIV-1 infection and AIDS, said monkey being infected with the virus, "SHIV-PNb (now renamed SHIV-KU-1) deposited with the NIH Reagent Program, McKesson BioServices, 685 Lofstrand Lane, Rockville, Md. 20850 as catalog number 3441, on Dec. 17, 1996."

The instant invention provides for a purified virus, and cell culture derived progeny of virus "SHIV-PNb (now renamed SHIV-KU-1) deposited with the NIH Reagent Program, McKesson BioServices, 685 Lofstrand Lane, Rockville, Md. 20850 as catalog number 3441, on Dec. 17, 1996."

The instant invention also provides methods for generating AIDS in a primate comprising administering to the primate viral isolate containing virus, the virus being passaged at least two times previously via primate bone marrow cells. In a preferred embodiment the virus has been passaged three times through bone marrow.

The instant invention also provides methods for generating AIDS in a primate comprising administering to the primate cell culture-derived progeny of the pathogenic virus SHIV-PPc. The instant invention also provides for methods for generating AIDS in a monkey comprising administering to the monkey viral isolate containing virus, or cell culture derived progeny of the virus "SHIV-PNb (now renamed SHIV-KU-1) deposited with the NIH Reagent Program, McKesson BioServices, 685 Lofstrand Lane, Rockville, Md. 20850 as catalog number 3441, on Dec. 17, 1996."

Thus the instant invention provides for a monkey model for AIDS, said monkey being treated by administering to the monkey viral isolate containing virus, the infective virus being passaged at least two times previously through monkey bone marrow. The invention also provides for a monkey model for HIV-1 induced disease, said monkey being infected with virus selected from the group consisting of SHIV-PPc, SHIV-PQc, and SHIV-PNb. The instant invention also embodies a monkey model wherein the virus used to generate the model is the cell culture derived progeny of a virus selected from the group consisting of SHIV-PPc, SHIV-PQc, and SHIV-PNb.

The instant invention also provides pathogenic SHIV virus generated by at least two successive passages of non, or low pathogenicity virus through primate bone marrow, and cell-culture derived progeny of the virus. Further, the instant invention also provides a method for generating a pathogenic SHIV virus comprising at least two successive passages of a non-pathogenic or low pathogenicity SHIV through primate bone marrow.

The instant invention provides methods for generating AIDS in a monkey comprising administering to the monkey viral isolate containing virus, the virus being passaged at least two times previously via monkey bone marrow. In a preferred embodiment, the invention provides for a method for generating AIDS in a monkey comprising administering to the monkey virus, or cell culture derived progeny from virus selected from the group consisting of SHIV-PPc, SHIV-PQc, and SHIV-PNb.

DETAILED DESCRIPTION OF THE PREFERRED EMBODIMENTS

Figure 1A:
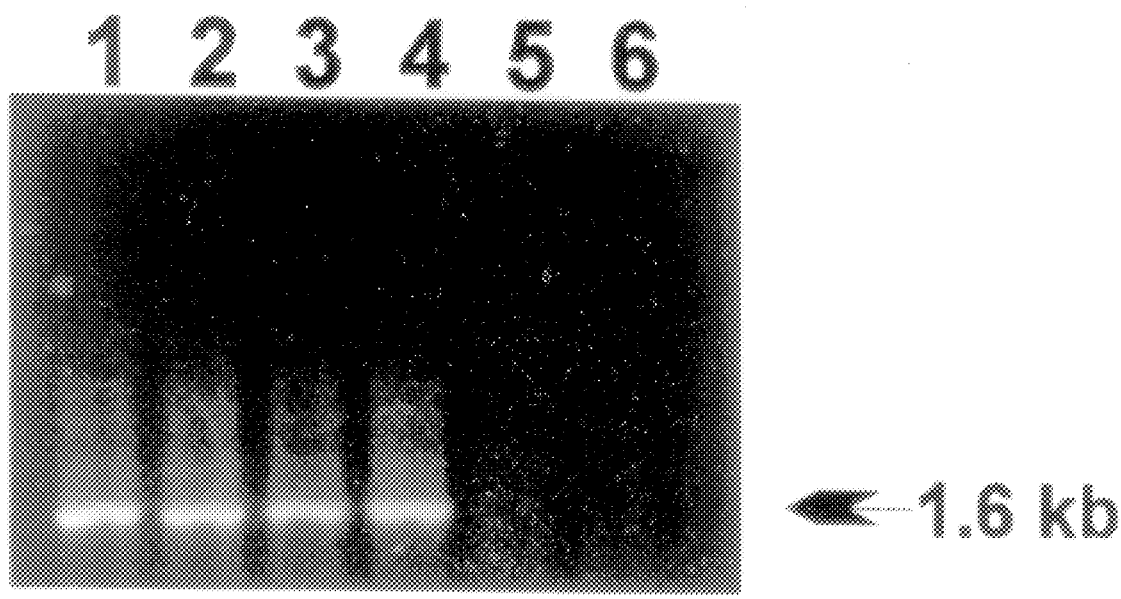
FIG. 1A shows a picture of an agarose gel showing PCR products from splenic tissues.

HIV-1 does not cause disease in any non-human species. Thus, there is no animal model system to evaluate the efficacy of strategies aimed at preventing or ameliorating disease caused by this virus. Since the virus envelope is thought to play a major role in pathogenesis, chimeric simian-human immunodeficiency virus (SHIV) consisting of the core of SIVmac and the envelope of HIV-1 were constructed, but these agents have not proven to be pathogenic. The instant invention provides a pathogenic SHIV generated in pig-tailed macaques and thus the development of the first animal model in which macaques inoculated with a lentivirus bearing the HIV-1 envelope developed loss of $CD4^+$ T cells and AIDS. Non-pathogenic SHIV was serially passaged 3 times in cohorts of 2 macaques using bone marrow to bone marrow transfers at 5, 5 and 16 weeks, respectively. The virus became more virulent with each passage. Virus replication was controlled effectively by $CD8^+$ T cells in animals in passages 1 and 2, but not in animals in passages 3 and 4. Virus resurgence, similar to that seen in HIV-1 infected humans, developed in the latter animals and was evident as high virus burden in T cells in blood and lymphoid tissues, plasma viremia and infection in the CNS. Three of four animals in the last 2 passages have developed $CD4^+$ T Cell loss. In one animal, the $CD4^+$ T cell count decreased from 2,000 to 35 cells per $\mu l$ in 26 weeks with development of AIDS. Two other animals have also developed declining $CD4^+$ T cell counts with increasing viral burdens, similar to that seen in the fatal case. All animals developed neutralizing antibodies to the virus. However, the passaged virus has become highly macrophage-tropic and in T cell lines, is less fusogenic than the original SHIV. Sequence analysis of the env gene of the pathogenic virus has shown multiple mutations, including some in the V3 loop.

The derivation of pathogenic SHIV began with a SHIV DNA encoding the env, tat, rev, and vpu genes of HIV-1 HXBc2 on a background of SIVmac239 (Li J et al., 1992, supra.; Obtained from Dr. Joseph Sodroski, Harvard University) and used to produce a stock of virus in CEMx174 cells transfected with the DNA. This stock virus was then used to begin passaging in young (nine months to 1 year old) rhesus (*Macaca mulatta*) and pig-tailed (*M. nemestrina*) macaques following a protocol which has been successfully used in the neuroadaptation of lymphocyte-tropic SIVmac239 in rhesus macaques (Sharma DP et al., 1992, *J. Virol.* 66: 3550–3556; all cited references are hereby incorporated by reference). Macaques were housed in AAA-LAC accredited facilities.

While virus have been previously adapted by passage of the virus through brain tissue, there has not been any reports of the attempted passage of virus through bone marrow tissue. The methods of the instant invention thus teach a unique method for generating pathogenic SHIV virus by the successive passage of a starting virus through bone marrow tissue.

The instant invention provides pathogenic virus for the creating animal models for HIV-1 infection that were generated by the passage of virus through bone marrow tissue. The virus isolated from animal PPc, now designated SHIV-PPc is a potent pathogenic virus which is capable of inducing HIV-1 disease in monkey, rapidly, and to final morbidity. It was apparent that the virus isolated from the prior passage animals were not as virulent as the SHIV-PPc. Virus SHIV-PPc has been studied in detail for virus burden and distribution. Virus SHIV-PQc, also a third passage virus, was found to be slightly less virulent than SHIV-PPc, in that final morbidity occurred 8 weeks after that of animal PPc. Yet the effects of the virus were similar in all other respects as far as modeling HIV induced disease. It was found that fourth passage virus SHIV-PNb was more virulent than SHIV-PPc, this virus bringing about AIDS in the animal in half the time as SHIV-PPc, 12 weeks as compared with 24 weeks. It is thus clear that with each additional passage, further more virulent strains can be generated. The major utility of such virulent SHIV virus is reducing the time scale for morbidity based measures of effectiveness. Thus major advantages of the instant animal model for human AIDS, are the use of simian subjects, and the shortened time to AIDS and death. The methods of the instant invention are applicable for the generation of pathogenic virus from non-pathogenic starting material, or for increasing the pathogenicity of slightly, or low-pathogenicity virus. The use of passage through bone marrow tissue is unique in the unexpected resulting increase in pathogenicity. The isolated virus from the bone marrow tissue, infected bone marrow cells, or cell culture derived progeny of the original bone marrow tissues once isolated provides potent material for the generation of animal models for HIV-1 induced disease, as well as starting material for the further passage of the virus through bone marrow or other tissues. This and other aspects of the instant invention are better illustrated by the examples below.

EXAMPLES

For the first passage (Passage 1), $1 \times 10^4$ TCID (Tissue culture infective dose) of SHIV virus was inoculated into the bone marrow (BM) of rhesus macaque 8A. Five weeks later, heparinized BM was obtained from this animal, mononuclear cells were purified over Ficoll-Hypaque gradients and $5 \times 10^7$ cells were inoculated into the femoral bone marrow of two pig-tailed macaques, PLc and PRc (Passage 2). Five weeks later, BM was aspirated from PLc and PRc (2 ml each), pooled, purified as above, and inoculated into the BM of two new pig-tailed macaques, PPc and PQc (Passage 3). Sixteen weeks later, bone marrow and splenic biopsies were obtained from macaques PPc and PQc and a mixture of splenocytes and BM cells from both animals were pooled and inoculated into two new pig-tailed macaques, PFb and PNb (Passage 4).

Figure 1B:
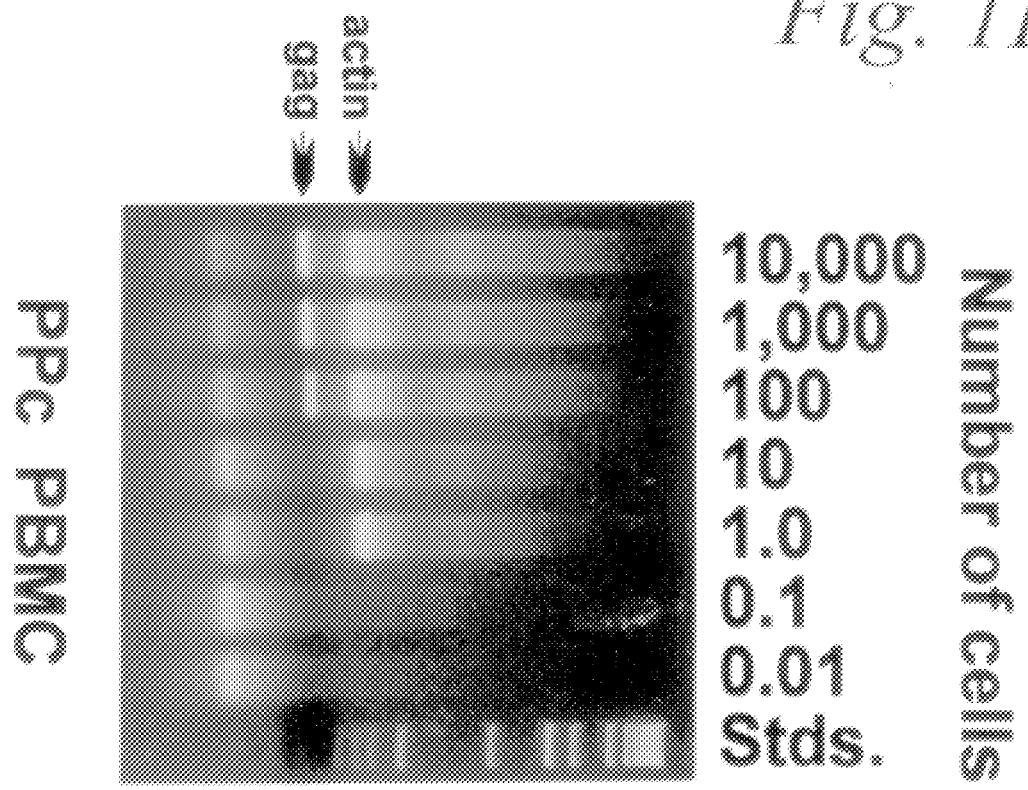
FIG. 1B shows a picture of an agarose gel showing PCR-Infected Cell Assay results.

Virus was isolated from peripheral blood mononuclear cells (PBMC) of all animals by co-cultivation with CEMx174 or C8166 cells, and confirmed to be SHIV in Western blot analyses using antisera specific for HIV-1 envelope and SIV gag proteins (data not shown). The identity of virus isolated from each animal was also confirmed by PCR amplification of a 1.6 kilobase DNA fragment from PBMC DNA, using oligonucleotide primers specific for sequences encoding the gp120 of HIV-1 HXBc2 but not SIVmac239 (FIG. 1A). As shown in Table 1, the frequency of infected cells (IC) in blood increased with successive passages, from 2 per $10^6$ PBMC in the Passage 1 animal to 1000 per $10^6$ PBMC in the Passage 4 pig-tailed macaques at 3 to 5 weeks post-inoculation (PI). The IC frequencies at 2 weeks PI were even higher ($10^4$ per $10^6$) in the Passage 4 animals. Examination of splenocytes from a portion of spleen biopsied from macaques PPc and PQc at 16 weeks showed $10^3$ infected cells per $10^6$, similar to the burden in PBMC at that time. Use of a polymerase chain reaction/infected cell assay (PCR/ICA) confirmed the infected cell frequency of $10^3$ to $10^4$ cells per $10^6$ spleenocytes (FIG. 1B). Histological analysis of spleen sections of both PPc and PQc showed massive loss of the cells in the T-cell rich areas around the germinal centers (FIG. 2).

FIG. 1A illustrates the results of PCR detection of viral DNA sequences from PBMC DNA. Total cellular genomic DNA was extracted from splenic tissue of pig-tailed macaques PPc and PQc and used as a template in nested polymerase chain reactions (PCR) to amplify either HIV-1 HXBc2 or SIVmac239 gp120 DNA sequences. For amplification of SIVmac gp120 sequences, the oligonucleotide primers used in the first round were 5'-GGCTAAGGCTAATACATCTTCTGCATC-3' (sense SEQ ID NO.:1) and 5'-ACCCAAGAACCCTAGCACAAAGACCCC-3' (antisense SEQ ID NO.:2), which are complementary to bases 6565 to 6591 and 8179 to 8205 of SIVmac239, respectively (Regier DA and Desrosiers RC, 1990, *AIDS Res. Hum. Retroviruses* 6: 1221–1231). One µg of genomic DNA was used in the PCR containing 2.0 mM MgCl$_2$, 200 µM each of the four deoxynucleotide triphosphates, 100 pM each oligonucleotide primer and 2.5 U Taq polymerase (Perkin-Elmer Cetus, Norwalk, Conn.). The template was denatured at 92 C. for 3 min and PCR amplification performed with an automated DNA Thermal Cycler (Perlin-Elmer Cetus) for 35 cycles using the following profile: denaturation at 92° C. for 1 min, annealing at 55° C. for 1 min, and primer extension at 72 C. for 3 min. Amplification was completed by incubation of the PCR for 10 min at 72° C. One µl of the PCR product from above was used in a nested PCR using the same reaction conditions as described above. For the second round of amplification, the nested set of primers were 5'-GTAAGTATGGGATGTCTTGGGAATCAG-3' (sense SEQ ID NO.:3) and 5'-GACCCCTCTTTTATTTCTTGAGGTGCC-3' (antisense SEQ ID NO.:4), which are complimentary to bases 6598 to 6624 and 8158 to 8184 of the SIVmac239 genome, respectively. For amplification of HIV-1 HXBc2 gp120 sequences, the oligonucleotide primers used in the first round were 5'-CAAAGAAAAATAGACAGGTTAATTGAT-3' (sense SEQ ID NO.:5) and 5'-AGTGCTTCCTGCTGCTCCCAAGAACCC-3' (antisense SEQ ID NO.:6), which are complementary to bases 6166 to 6192 and 7810 to 7784 of the HXBc2 genome, respectively (Fisher AG et al., 1985, *Nature* 316: 262–265). For the second round of amplification, the nested set of primers were 5'-GACTAATAGAAAGAGCAGAAGACAGTGGCA-3' (sense SEQ ID NO.:7) and 5'-GAACAAAGCTCCTATTCCCACTGCTCT-3' (antisense SEQ ID NO.:8), which are complimentary to bases 6194 to 6223 and 7780 to 7754 of the HXBc2 genome, respectively. The conditions for amplification of the HXBc2 gp120 sequences were the same as described for the SIVmac239. A 10 µl aliquot from each of the second round amplifications was run on a 0.8% agarose gel and bands visualized by staining with ethidium bromide. To confirm the specificity of the PCR products, the DNA in the gel was transferred onto nitrocellulose and hybridized with $^{32}$P-labeled gp120 DNA probes generated from the gp120 gene of either SIVmac239 or HIV-1 HXBc2 (data not shown). In FIG. 1A, Lanes 1–3 show: amplification using oligonucleotide primers specific for HIV-1 HXBc2 gp120 sequences from (lane 1) plasmid containing the SHIV genome, (lane 2) PPc spleen DNA, and (lane 3) PQc spleen DNA. Lanes 4–6 show: amplification using oligonucleotide primers specific for SIVmac239 gp120 sequences from (lane 4) a plasmid containing the complete SIVmac239 genome DNA, (lane 5) PPc spleen DNA, (lane 6) PQc spleen DNA. Amplifications of gp120 sequences using either set of oligonucleotide primers with DNA from uninfected animals, were negative (data not shown).

FIG. 1B illustrates the results from PCR amplification to determine virus-infected PBMC. A polymerase chain reaction infected cell assay (PCR-ICA) was used to determine the number of virus-infected cells in PBMC from macaque PPc. This assay has been described previously (Joag SV et al., 1994, *supra.*). Cell suspensions were diluted to $1\times10^7$, $1\times10^6$, $1\times10^5$, $1\times10^4$, $1\times10^3$, and $1\times10^2$ cells per ml, and cells were then lysed and digested. Two rounds of PCR amplification were used to detect SIV gag sequences. In the first round, oligonucleotide primers used were 5'-GATGGGCGTGAGAAACTCCGTCTT-3' (SEQ ID NO.:9) and 5'-CCTCCTCTGCCGCTAGATGGTGCTGTTG-3' (SEQ ID NO.:10) which are complementary to bases 1052 to 1075 and 1423 to 1450 of the SIVmac239 gag gene, respectively (Regier DA and Desrosiers RC, 1990, *supra.*). To standardize cell numbers, the fourth exon of β-actin was amplified with oligonucleotide primers 5'-TCATGTTTGAGACCTTCAACACCCCAG-3' (SEQ ID NO.:11) and 5'-CCAGGAAGGAAGGCTGGAAGAGTGCC-3' (SEQ ID NO.:12) (non-coding) complementary to published sequences (Nakajima-Iijima S et al., 1985, *PNAS (USA)* 82: 6133–6137). The PCR conditions were as given above. To increase the sensitivity of the reaction, 1 µl of the first PCR product was used as a template for a second amplification using the same conditions. The nested SIV primers used were 5'-GTTGAAGCATGTAGTATGGGCAGC-3' (SEQ ID NO.:13) and 5'-GCCTCAGGGCAGCGGAACCGCTCA-3' (SEQ ID NO.:14) which are complimentary to bases 1142 to 1165 and 1356 to 1382 of SIVmac239, respectively. The nested β-actin primers used were 5'-CCCCAGCCATGTACGTTGCTATCC-3' (SEQ ID NO.:15) and 5'-GCCTCAGGGCAGCGGAACCGCTCA-3' (SEQ ID NO.:16). Following the second round of amplification, a 10 µl aliquot was removed and run on a 1.5% agarose gel and bands visualized by staining with ethidium bromide. After the second round of amplification, the internal control (β-actin) yielded a 393 base pair band, whereas the amplified SIV gag sequence yielded a 240 base pair band.

Figure 2A:
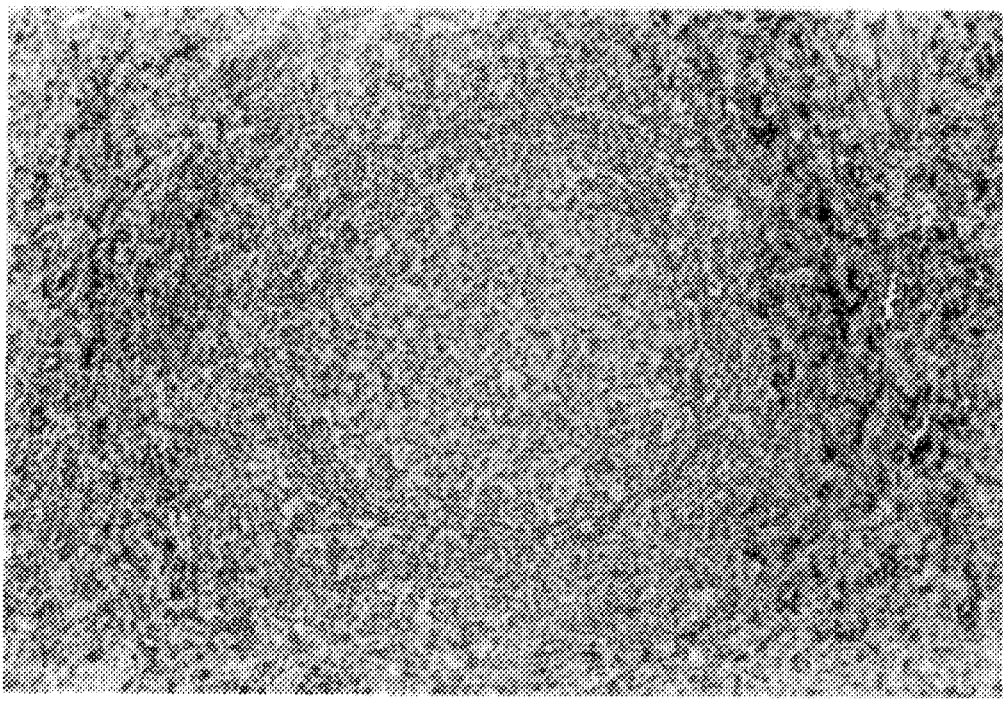
FIGS. 2A and 2B show pictures of histologic sections of spleen.
Figure 2B:
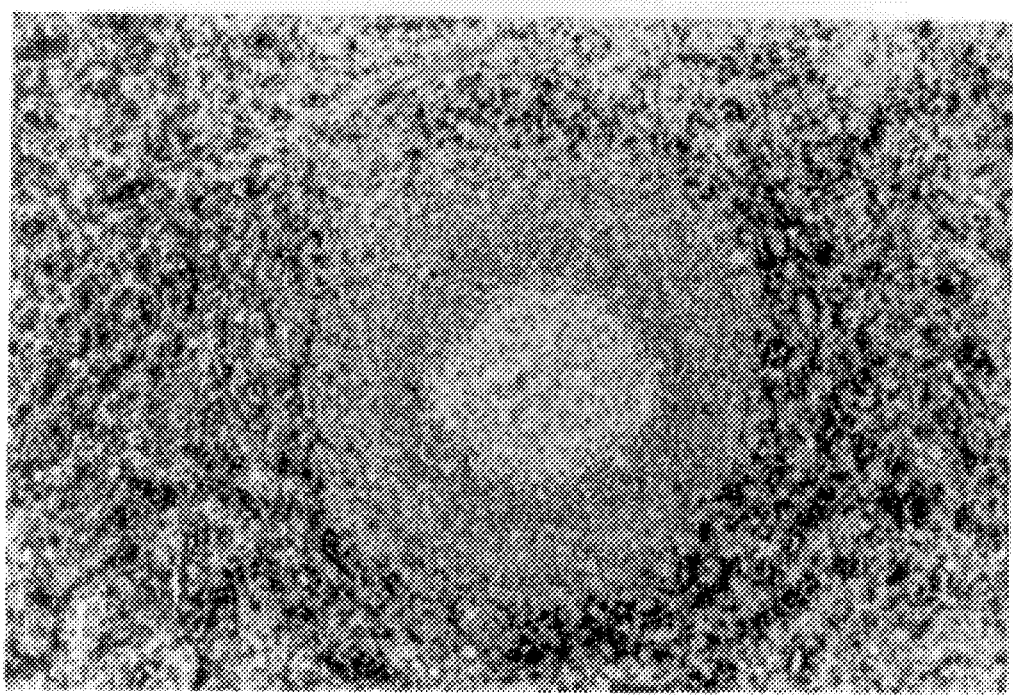

FIG. 2 shows paraffin-embedded histological sections of spleen biopsies from macaque PPc at 16 weeks post-inoculation (2A), and from an age-matched normal pig-tailed macaque (2B). There is a diffuse loss of cells from the mantle zone and marginal zone in PPc. Staining was H&E, magnification 66X.

An indication of the nature of the infection in mononuclear cells was obtained by cultivation of these cells in special media. Cultures of PBMC from all animals in macrophage-differentiation medium (Joag SV et al., 1994, *J. Leukoc. Biol.* 56: 353–357) containing M-CSF and GM-CSF yielded esterase$^+$ CD68$^+$ adherent cells that produced infectious virus, showing that macrophages in these animals were productively infected. Cultivation of mitogen-treated PBMC yielded infectious virus routinely in Passage 3 and Passage 4 animals, only occasionally in Passage 2 animals, but not in rhesus 8A (PHA/IL-2 culture, Table 1). Virus virulence increased further in the two Passage 4 animals, PFb and PNb. These two animals developed infectious plasma viremia and infectious cells in the cerebrospinal fluid during the first 6 weeks of infection. In addition, PBMC from both animals produced infectious virus when cultivated directly in maintenance medium containing IL-2 (100 U/ml), without activation of the cells with mitogen. This indicated that the infected cells had become activated in vivo and were producing virus, a finding consistent with the plasma viremia and invasion of the CNS with infected cells (Joag SV et al., 1994, *J. Med. Primatol.* 23: 108–116).

TABLE 1

Virus burdens and CD4$^+$ T-cell counts in
SHIV-infected Macaques 3 to 5 weeks post-inoculation.

| Passage | Macaque | Inf. PBMC per 10$^4$ | Inf. Virus PHA/IL-2 | Inf. Virus Plasma | CD4$^+$/μl | CD4$^+$/μl pre-inoc. |
|---|---|---|---|---|---|---|
| 1 | Rh. 8A | 2 | Neg | Neg | 2430 | 1320 |
| 2 | PLc | 10 | Neg | Neg | 680 | 2010 |
| 2 | PRc | 10 | Neg | Neg | 450 | 2830 |
| 3 | PPc | 10 | Pos | Neg | 140 | 1540 |
| 3 | PQc | 10 | Pos | Neg | 340 | 2570 |
| 4 | PFb | 100 | Pos | Pos | 1140 | 2240 |
| 4 | PNb | 1000 | Pos | Pos | 270 | 1940 |

The frequency of infectious cells in Ficoll-Hypaque purified mononuclear cells from blood of inoculated animals was determined by co-cultivating dilutions of the mononuclear cells with indicator C8166 or CEMx174 cell cultures and observing for CPE (cytopathic effect) daily for 7 days (procedure after Joag SV et al., 1994, *Virology* 200: 436–446). For PHA/IL-2 cultures, PBMC were cultured in medium containing mitogen (PHA-P, Wellcome, 1 μg/ml) for 2 days, then in medium containing IL-2 (100 U/ml) for 5 days, after which supernatant fluid was inoculated into C8166 or CEMx174 cell cultures for 7 days, examining for CPE daily (Joag SV et al., 1994, *supra*.). Plasma infectivity was determined by inoculating dilutions of plasma into C8166 or CEMx174 cell cultures for 7 days and examining for CPE daily (Joag SV et al., 1994, *supra*.). CD4$^+$ counts were assessed by flow cytometry (Joag SV et al., 1994, *supra*.).

All animals developed neutralizing antibodies to HIV-1 HXBc2, original SHIV, and SHIV isolated from macaque PPc, but not to SIVmac239. Neutralizing antibody titers varied from 1:20 to 1:160 using 10 to 20 TCID (Tissue culture infective dose) of virus against dilutions of the plasma (Joag SV et al., 1993, *Virology* 195: 406–412). The virus became highly macrophage-tropic during passage. Immunocytochemical analysis of cultures showed that whereas original SHIV caused infection in about 1% of inoculated macaque macrophages, the passaged virus (from PPc and PQc; Passage 3) caused infection in about 30% of the cells. Limited sequence analysis of gp120 clones derived from splenocytes of PPc and PQc revealed amino acid substitutions in both conserved and variable regions (data not shown). These changes include substitutions in the V3 region, to which determinants of macrophage-tropism of HIV-1 have been mapped.

The dynamics of pathogenesis varied from animal to animal, as expected. Table 2 shows a longitudinal study of one of the macaques, PPc, a Passage 3 animal. Following an initial drop during weeks 2 to 4 PI, the CD4$^+$ T-cell count recovered partially during weeks 12 to 18 PI, after which it fell again. The second decline in the CD4$^+$ count was associated with a sustained increase in virus replication, during which the frequency of infected cells in PBMC reached a level of $10^4$ per $10^6$ at week 18. Plasma viremia developed at week 23 and was accompanied by appearance of infected cells in the cerebrospinal fluid. This indicated virus invasion of the CNS during this period. Macaque PPc remained healthy until 20 week PI when rectal prolapse and intractable diarrhea developed, appearing initially as poorly formed, pasty feces and progressing to liquid diarrhea associated with *Trichuris trichuria* infestation. The animal also developed significant loss of weight and anemia (hemoglobin 7.4 g/dl), and was euthanized at 26 weeks, with a CD4$^+$ T-cell count of 28/μl. Studies on tissues collected at necropsy from this animal showed that the highest virus burden was present in the thymus. This finding supports the idea that loss of CD4$^+$ T-cells results from lysis of the cells in the periphery as well as at the source (Ho DD, et al., 1995, *Nature* 373: 123–126; Wei X et al., 1995, *Nature* 373: 117–122).

TABLE 2

Virus burden and CD4$^+$ T-cell counts in Macaque PPc.

| Week PI | CD4$^+$/μl | CD8$^+$/μl | % CD4$^+$ | Inf. PBMC per 10$^6$ | Plasma infec. (TCID/ml) |
|---|---|---|---|---|---|
| −1 | 1540 | 1490 | 37 | — | — |
| 2 | 100 | 1360 | 4 | 100 | 0 |
| 4 | 140 | 880 | 8 | 10 | 0 |
| 6 | 320 | 2020 | 9 | 10 | 0 |
| 8 | 310 | 1280 | 11 | 10 | 0 |
| 12 | 804 | 1675 | 12 | 100 | 0 |
| 18 | 643 | 2715 | 9 | 10000 | 0 |
| 20 | 265 | 2034 | 6 | 1000 | 0 |
| 22 | 164 | 2245 | 3 | 100 | 0 |
| 23 | 64 | 1973 | 1 | 1000 | 100 |
| 25 | 37 | 1154 | 1 | 100 | 0 |
| 26 | 28 | 832 | 1 | 10 | 0 |

CD4$^+$ and CD8$^+$ counts were assessed by flow cytometry, the frequency of infected cells in PBMC and the plasma infectivity were assessed as above in Table 1.

*Mycotic gastritis* and Trichuris infestation confirmed the case of full blown AIDS. PBMC, BM cells, splenocytes, and LN cells from this animal were cultured with Raji cells for 10 days to detect the presence of Type D retroviruses. The absence of CPE (Cytopathic effect) in Raji cell co-cultures and the normal CD8$^+$ counts, together with the lack of antibodies to Type D retroviruses, indicated that Type D simian retroviruses were not present in the animal. Similarly, lack of SIVmac env sequences in PPc virus DNA as determined by PCR, lack of SIV gp120 and gp41 proteins in PPc virus-infected cells as determined by immunoprecipitation and Western blot, and the failure of the animal to develop antibodies to SIV gp120 and gp41 as determined by immunoprecipitation and Western blot, indicated that SIV was not present in this animal.

In summary, these studies have shown that SHIV, whose env gene was derived from a laboratory strain of HIV-1, increased in virulence rapidly by passage of infectious bone marrow cells from animal to animal. Increasing virus burdens in PBMC, splenocytes, and bone marrow, development of plasma viremia, appearance of infectious cells in the CSF, progressive loss of CD4$^+$ T-cells from blood and spleen, severe infection in the thymus, and development of AIDS have all been demonstrated. The pathogenic SHIV model taught by the instant invention, provides the means for studying pathogenesis of HIV-1 infection in so far as the viral envelope contributes to the disease. It also provides a disease-causing challenge virus for evaluating the efficacy of HIV-1 envelope vaccines and anti-HIV-1 drugs.

The foregoing examples were meant by way of illustration and not by way of limitation. While the invention has been described with respect to certain specific embodiments, it will be appreciated that many modifications and changes may be made by those skilled in the art without departing from the spirit of the invention. It is intended, therefore, by the appended claims to cover all such modification and changes as fall within the true spirit and scope of the invention.

What is claimed is:

1. A macaque monkey treated by the administration to said monkey a virus isolate containing virus, said virus having been passaged in vivo at least two times previously through macaque bone marrow, wherein prior to the first passage said virus was originally a simian HIV (SHIV) virus containing at least one DNA sequence which encodes for a human HIV env protein, and wherein said virus infects said monkey causing said monkey to develop AIDS-associated symptoms within about 32 weeks of infection.

2. A macaque monkey infected with the virus SHIV-KU-1, wherein said virus causes AIDS-associated symptoms in said monkey within about 32 weeks of infection.

3. A macaque monkey as in claim 2, wherein the virus is the cell culture derived progeny of the virus SHIV-KU-1.

4. An SHIV virus which causes AIDS-associated symptoms in macaque monkeys, generated by at least two successive passages in vivo of viral isolate containing virus through macaque bone marrow, wherein prior to the first passage said virus was originally a simian HIV(SHIV) virus containing at least one DNA sequence which encodes for a human HIV env protein, and wherein said virus infects said monkey causing said monkey to develop AIDS-associated symptoms within about 32 weeks of infection.

5. A virus SHIV-KU-1 deposited with the NIH Reagent Program, McKeeson BioServices, 685 Lofstrand Lane, Rockville Md. 20850 as catalog number 3441.

6. A Cell-culture derived progeny of the virus of claim 4, wherein said virus causes AIDS-associated symptoms in macaque monkeys within about 32 weeks of infection.

7. A Cell-culture derived progeny of the virus of claim 5, wherein said virus causes AIDS-associated symptoms in macaque monkeys within about 32 weeks of infection.

8. A method for generating AIDS-associated symptoms in a macaque monkey, comprising administering to said monkey a viral isolate containing virus, said virus being passaged in vivo at least two times previously through macaque bone marrow, wherein prior to the first passage said virus was originally a simian HIV(SHIV) virus containing at least one DNA sequence which encodes for a human HIV env protein, and wherein said virus infects said monkey causing said monkey to develop AIDS-associated symptoms within about 32 weeks of infection.

9. A method for generating AIDS-associated symptoms in a macaque monkey comprising administering to said monkey viral isolate containing virus, said virus being SHIV-KU-1, wherein said virus infects said monkey causing said monkey to develop AIDS-associated symptoms within about 32 weeks of infection.

10. The method as in claim 9 wherein the virus is a cell culture derived progeny of SHIV-KU-1.

11. A method for generating an SHIV virus which causes AIDS-associated symptoms in macaque monkeys within about 32 weeks after infection, comprising manipulating an SHIV virus by at least two successive passages in vivo through macaque bone marrow, wherein prior to the first passage said virus was originally a simian HIV(SHIV) virus containing at least one DNA sequence which encodes for a human HIV env protein.

* * * * *